(12) United States Patent
Bhattacharjee et al.

(10) Patent No.: US 9,393,161 B2
(45) Date of Patent: Jul. 19, 2016

(54) CONVENIENT RECLOSEABLE PROTECTIVE DIAPER PACKAGE

(71) Applicant: The Procter & Gamble Company, Cincinnati, OH (US)

(72) Inventors: Gautam Bhattacharjee, Beijing (CN); Xiaoling Qi, Beijing (CN); Ruoxin Zhang, Beijing (CN); Alrick Vincent Warner, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/708,621

(22) Filed: May 11, 2015

(65) Prior Publication Data

US 2015/0238372 A1     Aug. 27, 2015

Related U.S. Application Data

(63) Continuation of application No. PCT/CN2013/085855, filed on Oct. 24, 2013, and a continuation of application No. PCT/CN2012/084376, filed on Nov. 9, 2012.

(51) Int. Cl.
| | |
|---|---|
| *B65D 85/16* | (2006.01) |
| *A61B 17/06* | (2006.01) |
| *A61F 13/551* | (2006.01) |
| *B65D 75/56* | (2006.01) |
| *B65D 33/25* | (2006.01) |
| *B65D 33/08* | (2006.01) |

(52) U.S. Cl.
CPC ....... *A61F 13/5511* (2013.01); *A61F 13/55105* (2013.01); *B65D 33/08* (2013.01); *B65D 33/25* (2013.01); *B65D 33/2508* (2013.01); *B65D 75/566* (2013.01); *B65D 85/16* (2013.01)

(58) Field of Classification Search
CPC .... B65D 33/08; B65D 33/25; A61F 13/5511; A61F 13/55105
USPC ......... 206/440, 494; 383/8, 10, 61.2, 63, 204, 383/209, 906
See application file for complete search history.

(56) References Cited

U.S. PATENT DOCUMENTS 5,851,071 A * 12/1998 Arnell ................ B65D 33/2533
                                                      383/209
5,934,470 A *  8/1999 Bauer ................... A61F 15/001
                                                      206/494

(Continued)

FOREIGN PATENT DOCUMENTS

CN        2010-95458 Y       8/2008
CN        202492006 U       10/2012

(Continued)

OTHER PUBLICATIONS

PCT International Search Report mailed Mar. 3, 2015 (7 pages).

(Continued)

*Primary Examiner* — Luan K Bui
(74) *Attorney, Agent, or Firm* — William E. Gallagher

(57) ABSTRACT

A package formed of polymer film and containing disposable diapers is disclosed. The package may include mating zip-lock components at a top opening that enable the package to be recloseable, and top portions that extend upwardly beyond the mating zip-lock components, the top portions each having a handle cut therethrough.

12 Claims, 11 Drawing Sheets

(56) References Cited

U.S. PATENT DOCUMENTS

| | | | |
|---|---|---|---|
| 6,318,555 B1* | 11/2001 | Kuske | B65D 75/522 206/494 |
| 7,342,314 B2 | 3/2008 | Bachmann et al. | |
| 7,655,830 B2 | 2/2010 | Flohr et al. | |
| 7,971,717 B2* | 7/2011 | Eilert | B65D 75/566 206/494 |
| 8,083,410 B2 | 12/2011 | Feist et al. | |
| 8,618,349 B2 | 12/2013 | Klofta | |
| 8,927,801 B2 | 1/2015 | Klofta | |
| 2004/0173490 A1* | 9/2004 | Otsubo | A61F 13/5511 206/440 |
| 2004/0211696 A1* | 10/2004 | Underhill | A61F 15/001 206/494 |
| 2005/0222550 A1* | 10/2005 | Mitsui | A61F 13/55115 206/440 |
| 2008/0292221 A1 | 11/2008 | Song | |
| 2011/0120897 A1* | 5/2011 | Takahashi | A61F 13/551 206/494 |
| 2011/0137274 A1 | 6/2011 | Klofta et al. | |
| 2011/0192749 A1* | 8/2011 | Hooyman | A61F 13/55115 206/440 |

FOREIGN PATENT DOCUMENTS

| | | |
|---|---|---|
| JP | 2001-031138 A | 2/2001 |
| WO | WO 2009-152021 A1 | 12/2009 |

OTHER PUBLICATIONS

PCT International Search Report mailed Aug. 22, 2013 (12 pages).
PCT International Search Report mailed Jan. 23, 2014 (12 pages).

* cited by examiner

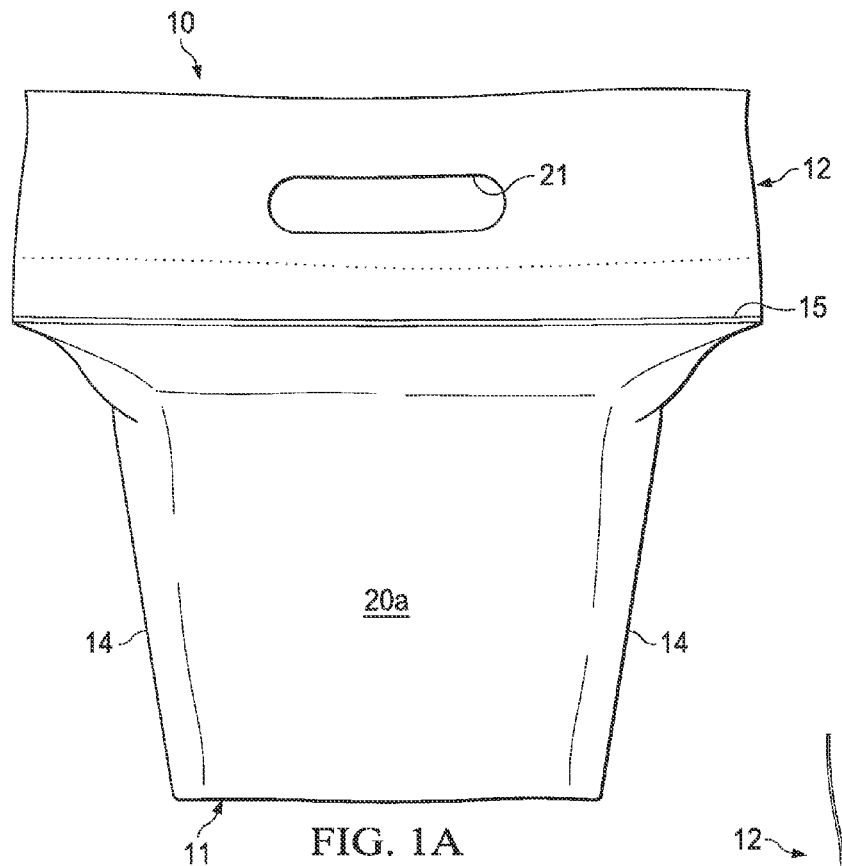
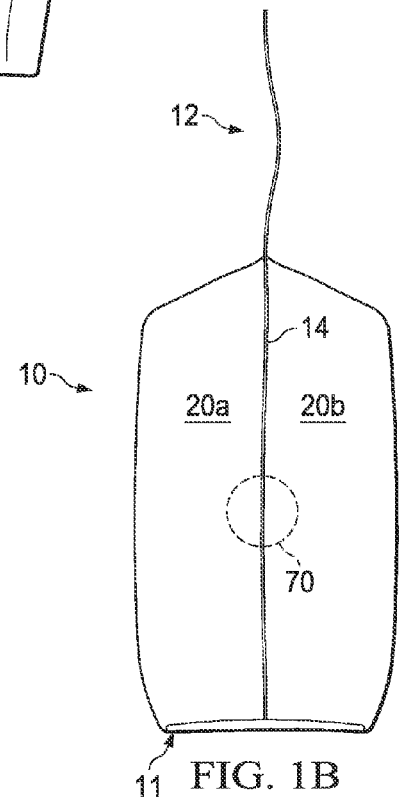
FIG. 1A
FIG. 1B

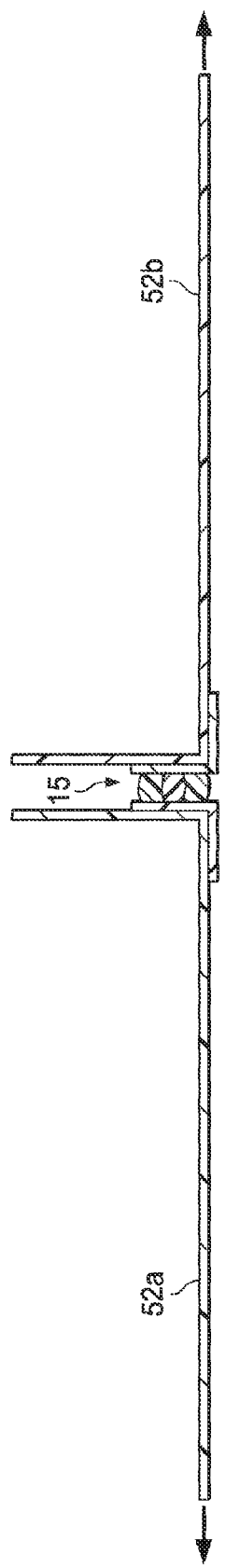

CONVENIENT RECLOSEABLE PROTECTIVE DIAPER PACKAGE

FIELD OF THE INVENTION

The present invention relates to recloseable packages for disposable diapers.

BACKGROUND OF THE INVENTION

Currently, disposable absorbent articles such as disposable diapers are sold in packages in a variety of configurations. In one configuration, a selected number of diapers are folded approximately in half along their lateral axes and collected and somewhat compressed in stacks that are roughly block-shaped, which are then enclosed in retail packages formed of polymer film. A typical package is also roughly block-shaped, and may have a line of perforations in the film partially or entirely circumscribing one side or end of the package, to facilitate opening of the package by tearing along the performations, thereby enabling access to the diapers within by the consumer.

Such packages, while relatively neat, compact and stackable for purposes of shipment and retail display, may be less than satisfactory for consumers in some circumstances. First, particularly for packages with larger counts of diapers, the package may be bulky and awkward for a consumer to carry. Second, once the package is opened, the supply of diapers in the package that remain for future use may be exposed to humidity, dust and dirt through the opened package, before they are used. Many current disposable diapers have absorbent cores containing particles of superabsorbent polymer. Some current disposable diapers have moisture-activated wetness indicators. Particularly in areas having high humidity, humid storage conditions may be present in the consumer's home. In humid storage conditions, superabsorbent particles can absorb water from the atmosphere over time, and impart an undesirably damp feeling to the diaper before its use. Wetness indicators can absorb water and be undesirably partially activated or rendered less effective. In dusty or dirty storage environments, the supply of diapers can be contaminated with dust or dirt. Any and all of these conditions and events may reflect negatively on the product to the consumer, and regardless of that, are deemed undesirable. Nevertheless, this shortcoming in diaper packages has existed.

Accordingly, there is an opportunity for improved diaper packaging that addresses these conditions.

DESCRIPTION OF THE DRAWINGS

FIG. 1A is a front view of a package of diapers.
FIG. 1B is a side view of a package of diapers.

FIG. 9 is a schematic illustration of the manner of pulling the specimen illustrated in FIGS. 7 and 8 for the Inside Opening Resistance measurement method.

DETAILED DESCRIPTION OF THE INVENTION

Figure 2:
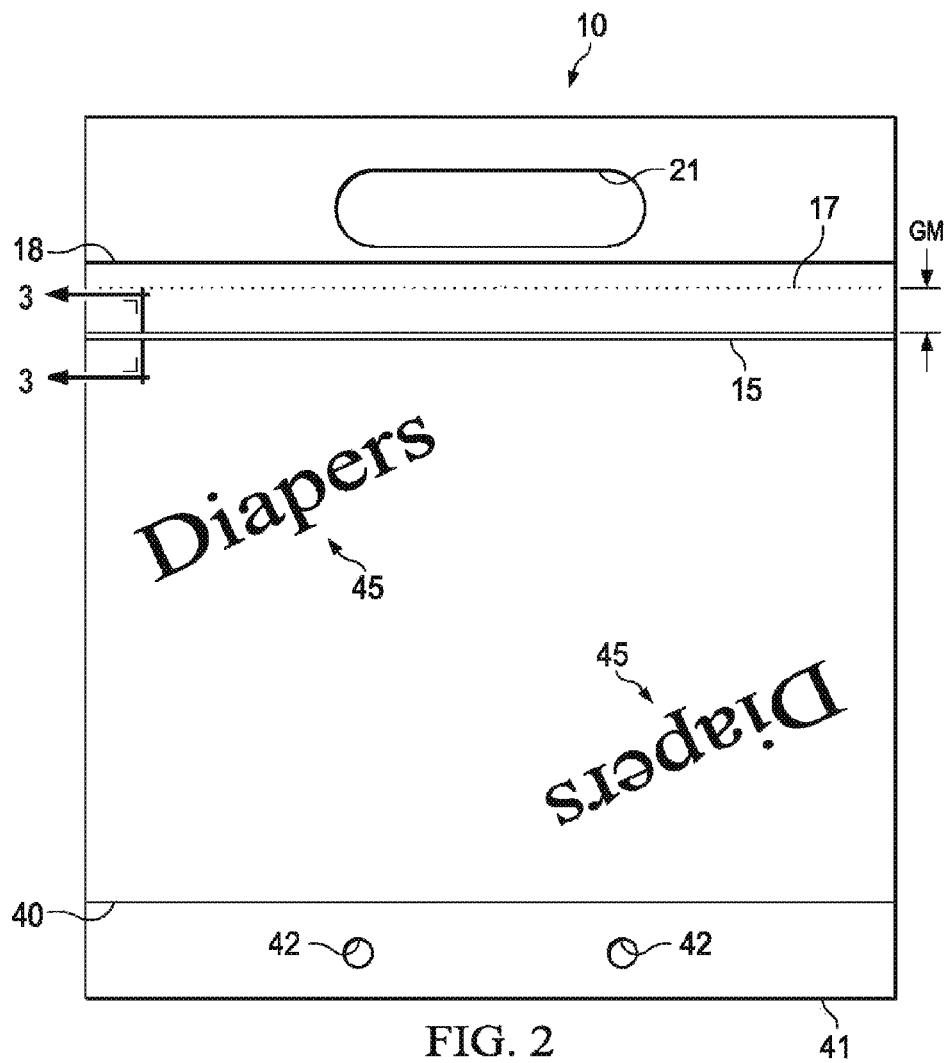
FIG. 2 is a schematic front view of a diaper package.

Relative positional terms (e.g., "bottom," "top," "side," "upper," "lower," "horizontal," "vertical," etc.) are used herein with respect to the orientation of the examples as depicted in the Figures.

"Absorbent polymer material," "absorbent gelling material," "AGM," "superabsorbent polymer" "superabsorbent material," and "superabsorbent particles" are used herein interchangeably and refer to particles of cross linked polymeric materials that can absorb at least 5 times their weight of an aqueous 0.9% saline solution as measured using the Centrifuge Retention Capacity test (EDANA 441.2-01).

Examples of packages as described herein are directed toward packages containing quantities of disposable diapers. Examples described herein may be particularly useful to package diapers that include absorbent cores that contain quantities of AGM, for purposes of imparting absorbency and liquid exudate isolation and storage capacity. Examples described herein may also be particularly useful to package diapers that include wetness indicators that respond to the presence of, or increase in, wetness or moisture within the diaper structure and provide visible signals of the same (such as a change of color of an area or feature of the diaper. Non-limiting examples of these types of diapers are described in PCT applications nos. WO2011/071807; WO2010/120706; WO2010/120705; WO2009/152021; and WO2006/017716; European patent application no. EP 1 624 002; U.S. patent application publication no. US2006/0030829; and U.S. Pat. No. 7,655,830.

Referring to FIGS. 1A and 1B, a retail package 10 of diapers may be formed of a polymer film. The film may be a single layer, or may have two or more layers. For example, the film may be formed of a single layer polyethylene film. Polyethylene may be deemed to have a desirable combination of relatively low material cost, strength and weldability at relatively low temperatures, and so may be deemed desirable. A multi-layer film also may have, for example, an outer layer formed of a first polymer and an inner layer formed of a second polymer. (As used herein, the terms "outer layer" and "inner layer" refer to the positioning of the layer relative the inside and the outside of the finished package; thus, the "inner layer" faces the contained product, and the "outer layer" faces outward and is visible to the consumer.) If packaging machinery forms welds in the film that join the film stock to itself by applying heat that causes the film to weld or fuse to itself, it may be desirable that the inner layer be formed of a polymer that has a lower melting temperature than that of the polymer used to form the outer layer. This enables heat energy to be applied to a degree sufficient to heat the inner layer and cause it to weld or fuse to itself, but not sufficient to cause undesired melting and deformation of the outer layer. The outer and inner layers may be co-formed (such as by coextrusion), or in another example, may be separately formed and then laminated together following their formation, by use of a suitable laminating adhesive. In this latter example, an advantage provided is that one of the layers may be printed on one side before lamination. Following that, the printed side may be faced inward (facing the other layer(s)) during lamination, such that it is protected by the other layer(s) from abrasion and wear in the finished film product, thereby preserving the integrity of the printed images, graphics, verbal content, etc. A suitable multilayer film may be formed of one or more polyolefins, such as polypropylene and polyethylene. In one example, the stock film may have at least two layers, including a first layer of polyethylene and second layer of polypropylene. In one example, a layer formed of polypropylene having a first relatively higher melting temperature, and a layer of polyethylene having a second relatively lower melting temperature, may be used to form the outer and inner layers, respectively.

Package 10 may be configured as a bag structure, having a welded bottom end portion 11 and a top end portion 12. (Herein, "weld" or "welded" refers to a union between distinct portions effected by thermal fusing and bonding, of the respective portions, which cannot be separated without substantial destruction to the remainder of one or both joined portions. A "frangible weld" is a union between distinct portions which may be broken apart and separated without substantial destruction to the remainder of either of the joined portions.) Preferably the bag structure has front and rear panels which are each formed of continuous sections of film joined at welded side seams 14. This provides a structure that neatly and efficiently accommodates a two-part zip-lock closure system, discussed below. Bottom end portion 11 may be formed with gussets so as to give the bag structure a roughly block shape and roughly flat bottom when packed with a roughly block-shaped stack of diapers, making the package suitable for standing as on a retail display shelf.

Figure 3A:
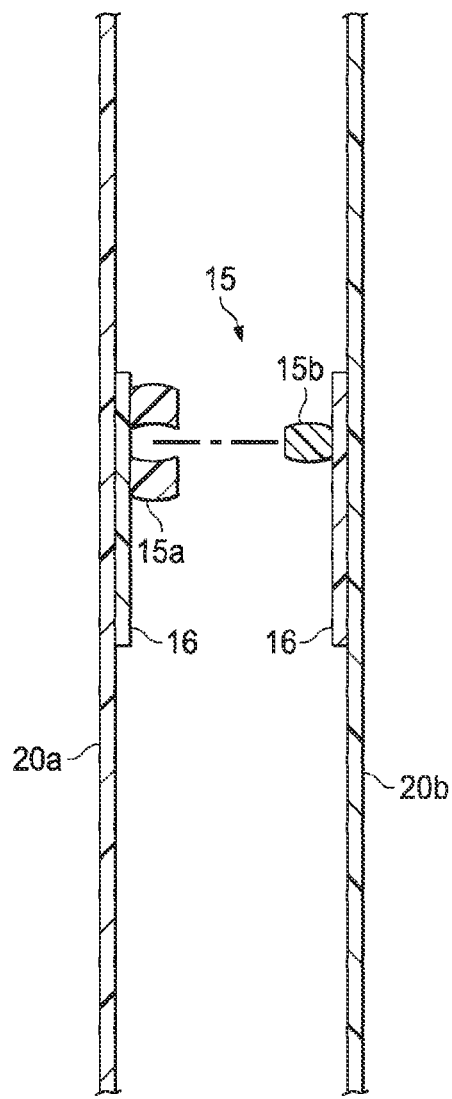
FIG. 3A is a schematic cross section taken at line 3-3 in FIG. 2, shown with zip-lock closure mechanism components disengaged.
Figure 3B:
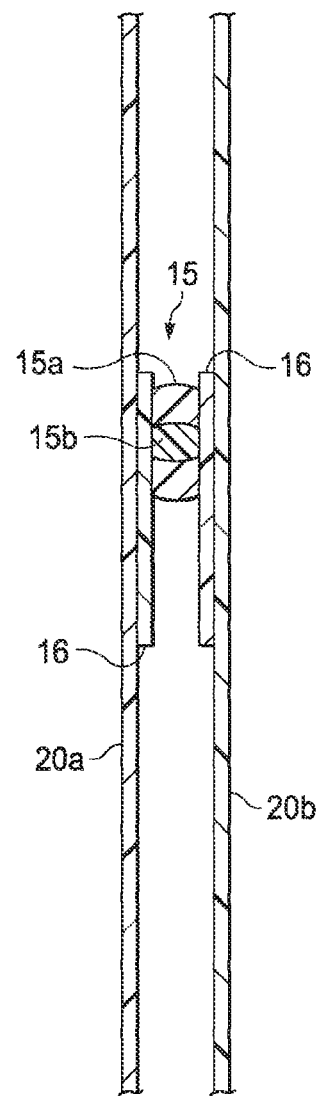
FIG. 3B is a schematic cross section taken at line 3-3 in FIG. 2, shown with zip-lock closure mechanism components engaged.

Referring to FIGS. 1A, 2, 3A and 3B, the top of the bag structure may include a zip-lock closure mechanism 15. Referring to FIGS. 3A and 3B, zip-lock closure mechanism 15 may include two linear, extruded polymer (e.g., polyethylene) components 15a, 15b with respective cooperating male and female cross sections, which may be integrally extruded with, or otherwise bonded to, strip substrate material 16. Strip substrate material 16, in turn, may be welded or adhesively bonded to, respectively, interior surfaces of the front and rear panels 20a, 20b, in opposing positions disposed to enable neat closure of the bag by pressing the zip-lock closure mechanism components together into a mated configuration as shown in FIG. 3B. Zip-lock closure mechanism components are exemplified by ZIPLOC brand systems on storage bag products from S.C. Johnson & Son, Inc., Racine Wis., but are available from a number of sources in various configurations and sizes. They are recloseable by the consumer, and may be effective barriers against entry of dust and dirt, and, for sufficient periods of time, substantial entry of moisture. Thus, the consumer can be provided with a recloseable package structure for keeping a supply of purchased diapers relatively clean and dry. In order to provide an effective moisture barrier, it may be desired that the zip-lock closure mechanism and top portions of the package be configured such that the zip-lock mechanism effectively closes the entire opening into the package, i.e., there are no gaps at, e.g., the sides or ends of the openable end of the package that are either not welded or otherwise held shut, or are not closeable via the zip-lock closure mechanism.

Preferably, no other weld or closure mechanism directly joins front and real panels 20a, 20b between side seams 14, proximate the opening, between the position of the zip-lock closure mechanism 15 and the top of the package contents. For compatibility and strength, the package and the zip-lock components may each be formed of at least 50 percent by weight of the same polymer, preferably formed of the same polymer.

In modern diaper packaging, a pre-determined number of diapers are folded, stacked, and compressed, prior to being enclosed in retail packages formed of polymer film. For purposes of efficiency in shipment, storage, and display, a certain amount of compression is applied to the stack of diapers. The amount of compression to be applied may be determined according to the number of diaper pads to be included per package, and in consideration of the influence of the compression force applied to the diaper. The in bag compression of the package of the present invention is typically in the range of from 1000 Pa to 10000 Pa, as measured according to the method set forth below. The package of the present invention comprises a zip-lock component which accommodates diapers which are compressed to such degree.

Zip-lock closure mechanism components are available and may be selected so as to provide varying degrees of resistance to opening separation (opening resistance). For a package of diapers, preferably the zip-lock closure mechanism as disposed in the bag, has an inside opening resistance sufficient to resist outwardly-directed forces in the panels, arising during carrying, that may tend to urge the zip-lock closure mechanism to separate and open. At the same time, opening resistance should not be so great as to make the zip-lock closure mechanism unacceptably difficult for the consumer to disengage to open the package. It is believed that an inside opening resistance from 0.79 N/cm to 48 N/cm, more preferably from 5.5 N/cm to 39 N/cm, and still more preferably from 10 N/cm to 29 N/cm will be sufficient for most diaper packages and will not prove unacceptably difficult for a consumer to open. Inside opening resistance of a zip-lock closure mechanism of a package of diapers is measured according to the method set forth below.

Figure 10A:
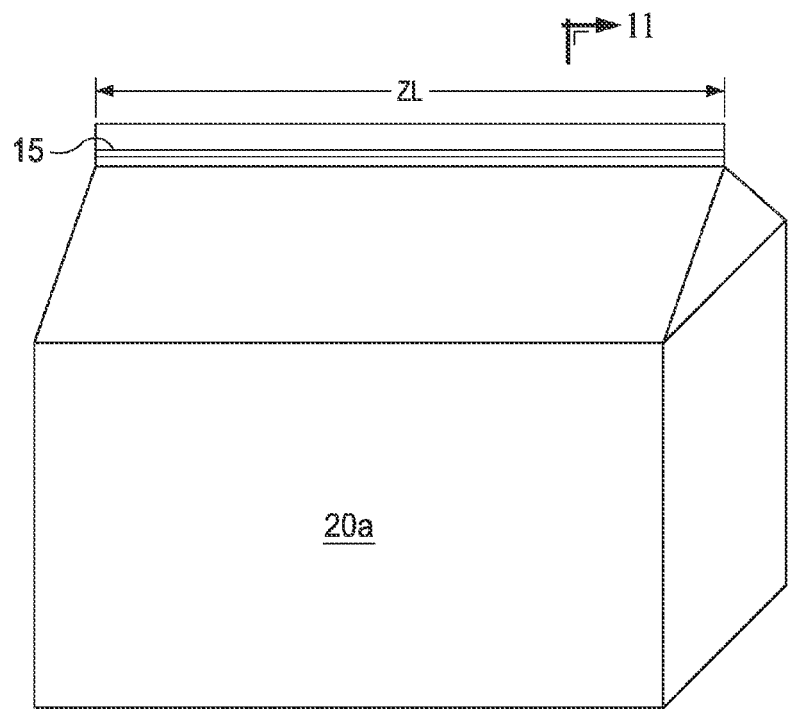
FIG. 10A is a schematic perspective view of a diaper package of one configuration.
Figure 10B:
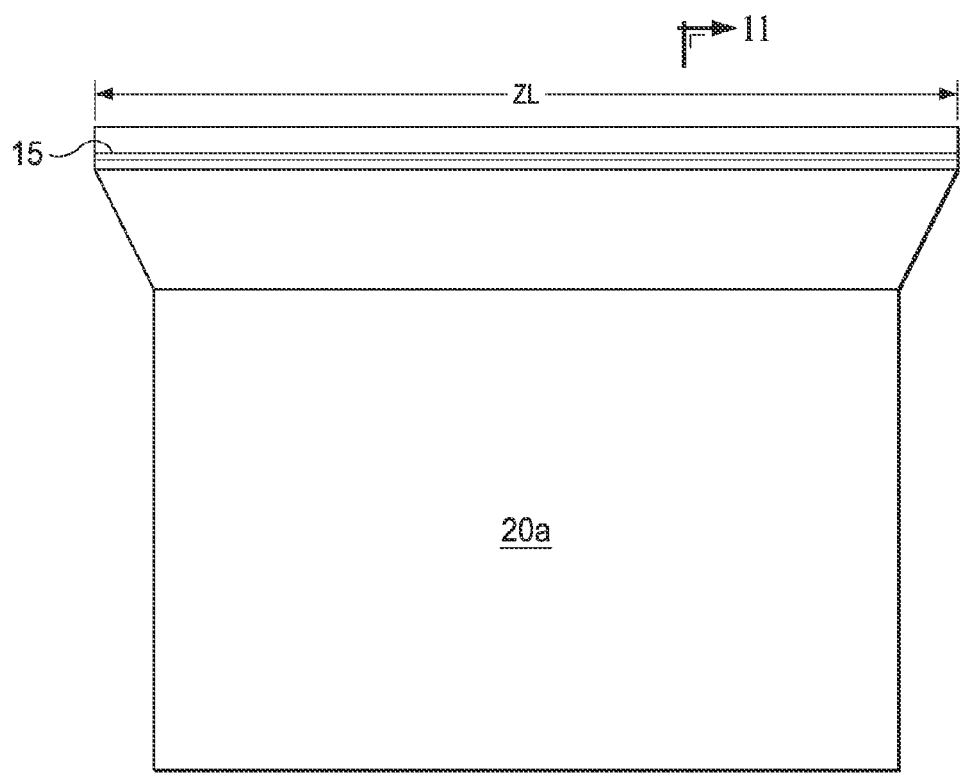
FIG. 10B is a schematic front view of a diaper package of an alternative configuration.
Figure 11:
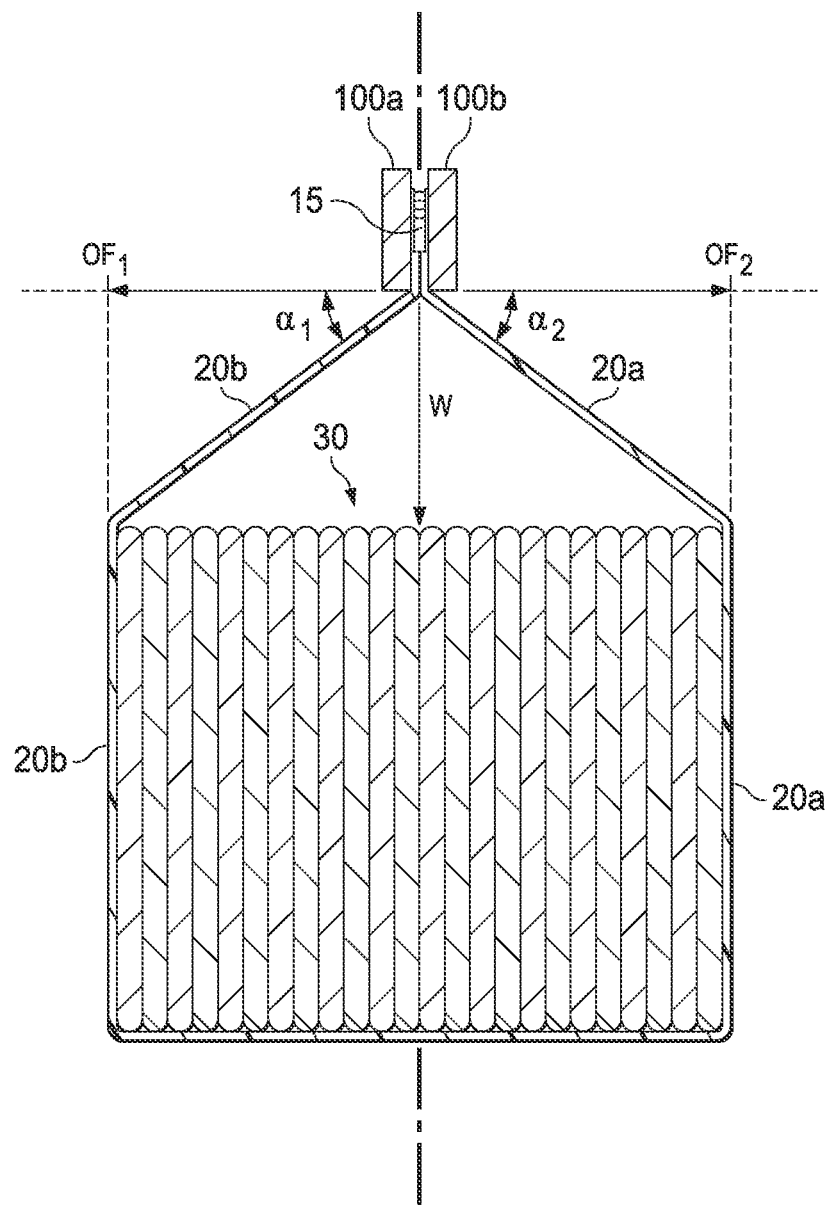
FIG. 11 is a schematic cross-sectional view of either of the diaper packages of FIG. 10A or 10B, depicted suspended by a gripping clamp.

To enable what is believed to be a more likely successful selection of a suitable zip-lock mechanism for purposes of, e.g., balancing resistance to inadvertent opening during carry with consumer convenience and acceptance, it may be desirable to configure the shape and dimensions of the package such that the aforementioned inside opening resistance is observed. Referring to FIGS. 10A, 10B and 11, it can be seen that the overall weight W of a diaper package will be translated to outwardly-directed horizontal force components $OF_1$ and $OF_2$ by the upper portions of panels 20a and 20b, when the package is suspended in the grip of, e.g., a person's fingers. Outwardly-directed force components $OF_1$ and $OF_2$ each equal the horizontal separating force (opening force) OF that must be withstood by the zip-lock mechanism 15 in a closed configuration during carry, to avoid separating and opening. Without intending to be bound by theory, it is believed that the opening force OF (N) is approximately distributed along the openable length ZL (cm) of the zip-lock mechanism. Namely, OF/ZL (N/cm) may be adjusted to meet the Inside Opening Resistance mentioned above.

Still referring to FIG. 11, as noted, opening force OF is equal to either of the horizontal force components $OF_1$ and $OF_2$, where:

$$OF_1 = OF_2 = W(\tan^{-1}\alpha_1)/[1+(\tan^{-1}\alpha_1/\tan^{-1}\alpha_2)], \text{ or}$$

$$OF_1 = OF_2 = W(\tan^{-1}\alpha_2)/[1+(\tan^{-1}\alpha_2/\tan^{-1}\alpha_1)],$$

where
W is the average weight of 10 sample packages of interest expressed in Newtons; and
Top Angles $\alpha_1$ and $\alpha_2$ are the angles formed by the respective upper portions of the front and rear panels with horizontal, where they extend between the respective upper front and rear edges of the stack of contained diapers 30 and the bottom-most edge of the inwardly-protruding portion of the mated zip-lock mechanism 15.

Accordingly, the suitable Top Angles $\alpha_1$ and $\alpha_2$ and openable length ZL (cm) may be determined according to the overall weight W (N) of the package. It should be noted that for any particular package, $\alpha_1$ and $\alpha_2$ may be equal, or approximately equal, or may differ, for example, where manufacturing, diaper stacking and compression, and packaging variations may result in differing lengths and/or angles of the respective upper portions of panels 20a, 20b (where "length" here is the length of the upper portion of a panel 20a or 20b in cross section as shown by way of example in FIG. 11). Top Angles $\alpha_1$ and $\alpha_2$ may be from 5 to 75 degrees, preferably from 15 to 75 degrees.

As suggested in, e.g., FIGS. 1A and 2, front and/or rear panels 20a, 20b may extend upwardly beyond the zip-lock closure mechanism. This provides respective margins of extra material above the zip-lock closure mechanism through which a handle cut 21 through one or both panels may be made. Handle cut 21 forms a carrying handle opening in the panels at the top of the package, enabling easy one-handed carry. Handle cut 21 may be oval shaped as suggested, or may be rectangular, circular, elliptical, oval, ovaloid, race-track shaped, rounded-rectangle shaped, etc. When handle cut 21 defines a shape of material cut out from the panel(s), preferably the shape has no sharp corners with vertices pointing horizontally or upwardly as would promote tear propagation from stresses resulting from carrying the package. It may be desired that both panels 20a and 20b have these upward extensions, with respective handle cuts that are substantially aligned with each other. This will provide a handle structure in both of the front and rear panels to support the weight of the package during carrying, and thereby more evenly distribute and balance stresses in the package structure, and help reduce a localized concentration of stresses along the zip-lock mechanism that could make an inadvertent and unwanted opening of the zip-lock closure mechanism more likely.

Figure 5:
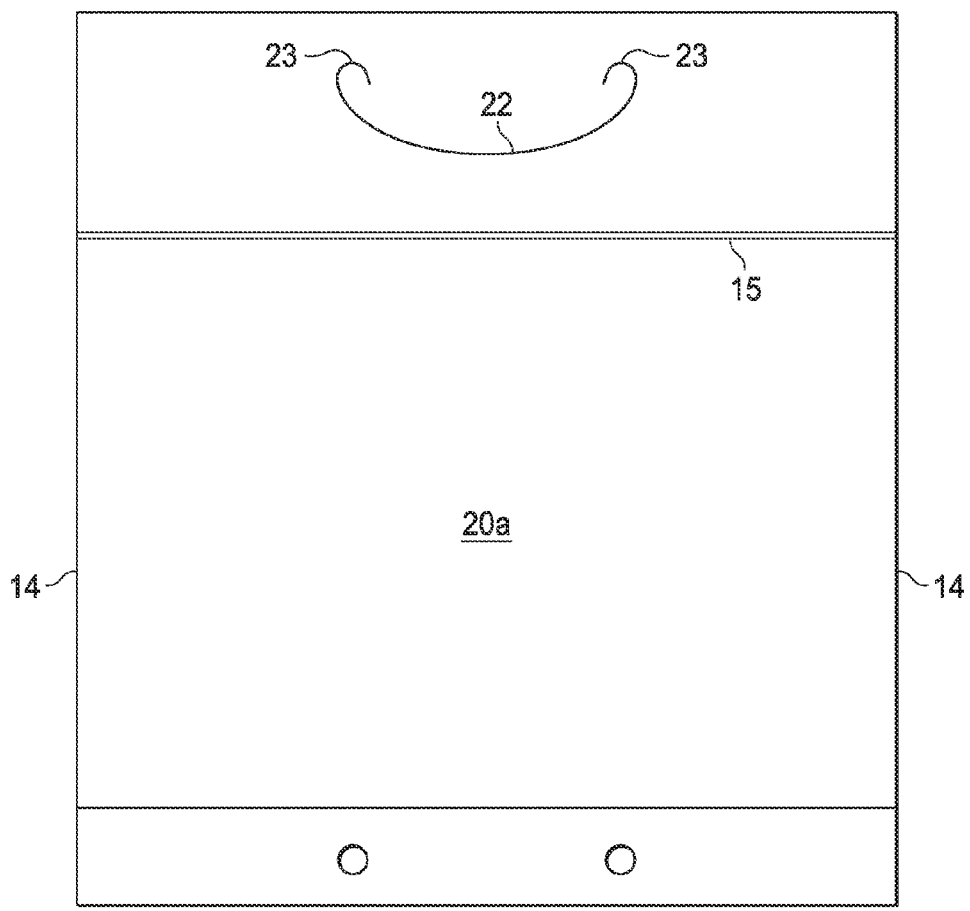
FIG. 5 is a schematic front view of a diaper package with an alternative handle cut configuration.
Figure 6:
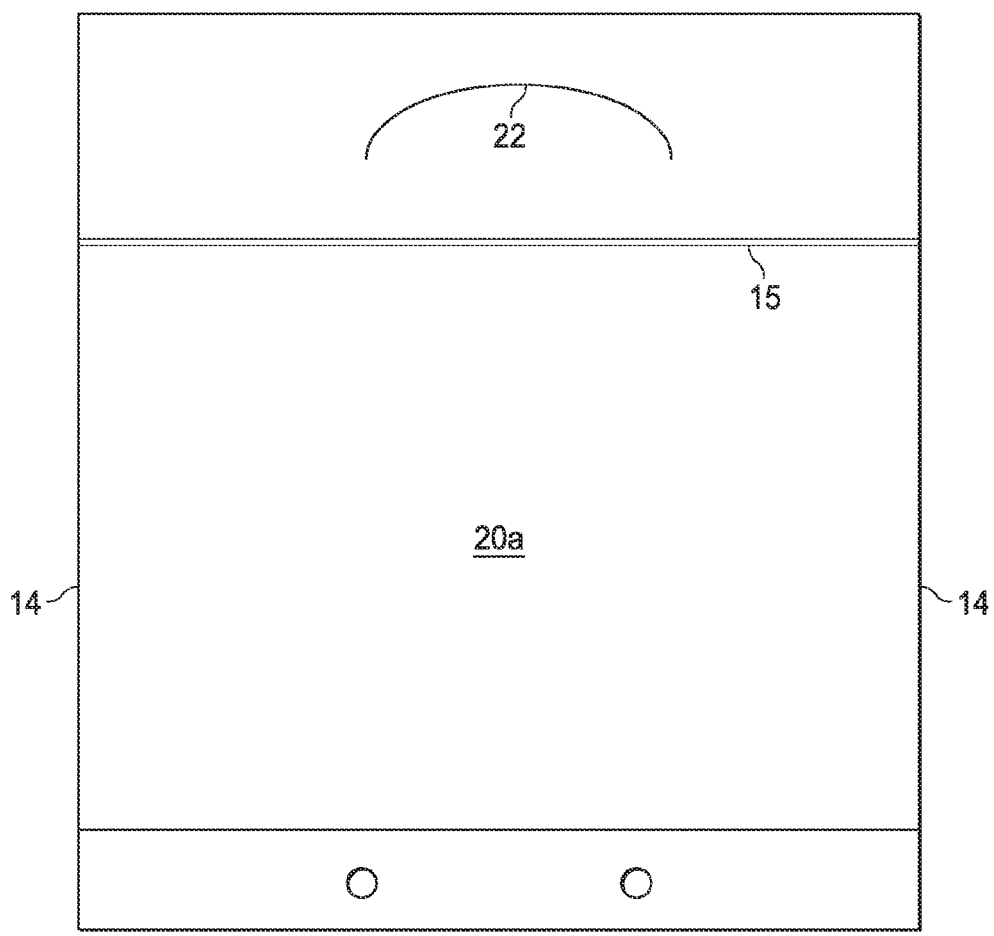
FIG. 6 is a schematic front view of a diaper package with another alternative handle cut configuration.

In another possible example illustrated in FIG. 5, the handle cut does not outline a shape of material cut out from the panel(s), but rather, is a partial "leaf" cut that allows creation of a handle opening through the panels when fingers are inserted thereabove through the panel(s) proximate the cut. An advantage provided by a leaf cut is that it eliminates creation of waste cutout material during manufacture of the package, and the necessity for a system to collect and dispose of the waste. As suggested in FIG. 5, a leaf cut 22 may include stress relief turns 23 proximate its terminal ends, which serve to reduce or avoid concentration of stress at the terminal ends at the cut, and resulting promotion of tear propagation, when the handle is under stress during carry. With a stress relief turn the terminal end of the cut generally points downwardly (i.e., lies lower than the immediately proximate portion of the cut that it terminates), but precise sizing and configuration of the stress relief turns would be a matter of design choice and routine optimization. In another example depicted in FIG. 6, a leaf cut 22 may have terminal ends pointing downwardly as shown. In the examples in FIGS. 5 and 6, the leaf cuts 22 have in common that their terminal ends generally point downwardly, reducing or avoiding concentration of tearing stress proximate the terminal ends. (A terminal end of a cut "points downwardly" when a line tangent to the curve of the cut at the terminal end is not horizontal, and the portion of the cut immediately proximate the terminal end lies above the terminal end.)

Preferably handle cut 21 or 22 is at least as wide or slightly wider than the average consumer's hand, e.g., at least 75 mm, but it may also be narrower if, for example, designed only to accommodate one or two fingers to carry the package. It will be appreciated that handle cut 21 or 22 may have the alternative form of a path of perforation, path of scoring or other path of weakness in the front and rear panels, such that the front and rear panels are not entirely cut through along the handle cut. In this alternative, a handle opening may be formed at the handle cut by pushing the fingers or another object against the panels adjacently above or below the cut, causing the film of the panels to tear along the path of weakness and create a handle opening.

Figure 4A:
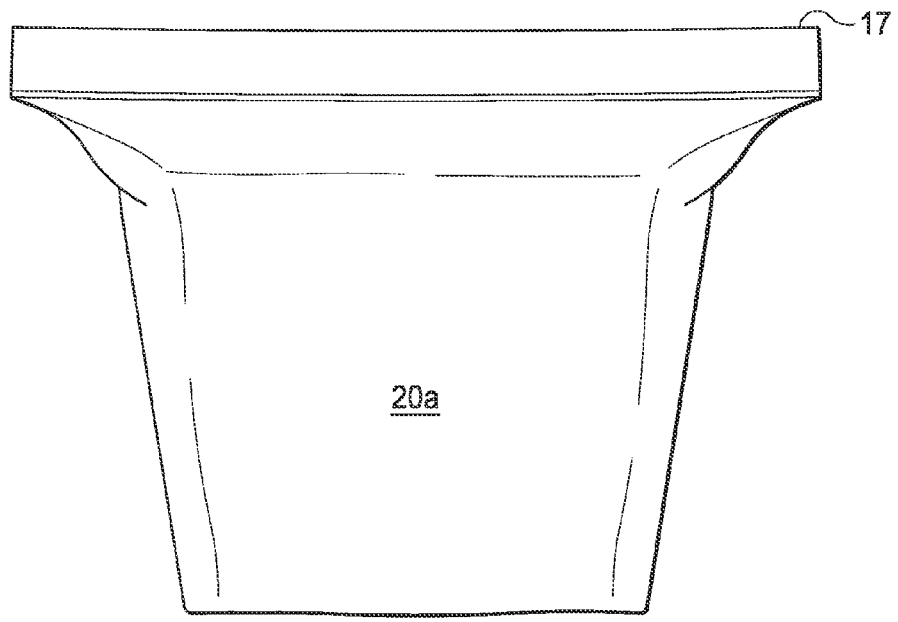
FIG. 4A is a front view of the package of diapers shown in FIG. 1A, with the handle portion removed.
Figure 4B:
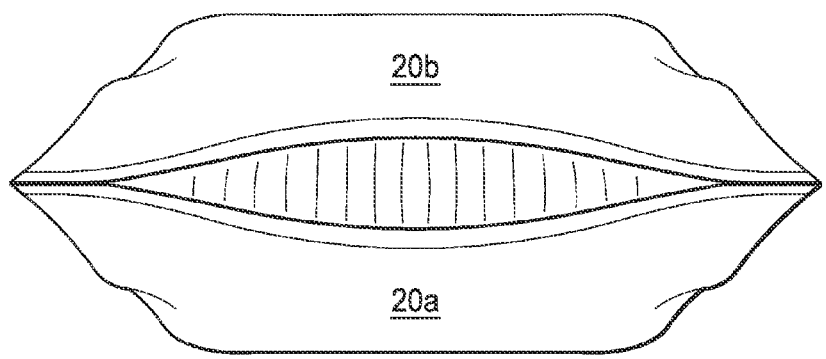
FIG. 4B is a top view of the package of diapers shown in FIG. 1A, with the handle portion removed, and in an opened state.
Figure 4C:
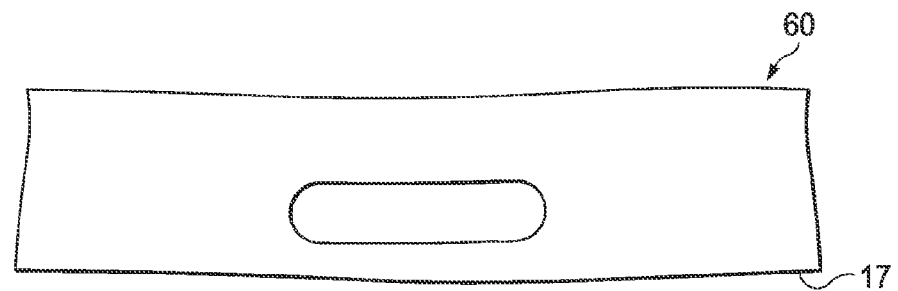
FIG. 4C is a front view of the removed handle portion of FIG. 1A.

Referring again to FIG. 2, front and/or rear panels 20a, 20b may have a line(s) of weakness 17 partially or entirely therethrough and extending partially or entirely across the package at a location above the zip-lock closure mechanism. The line(s) of weakness may be formed of a line of perforations or a line of partial scoring, such as controlled laser scoring, in the film. This provides a mechanism for the consumer to tear the handle structure 60 entirely away from the package along the line(s) of weakness following purchase, as in FIG. 4C. The line of weakness 17 may have an average tear resistance of from 10 N to 50 N. Where such a tear-away feature is included, however, the grasp margin GM of front and rear panel material left behind and above the zip-lock closure mechanism 15 at at least one location therealong (preferably at least between 33 and 67 percent of the horizontal length of the mechanism) is preferably at least 5 mm, more preferably at least 7 mm, and still more preferably at least 10 mm. (Grasp margin GM is measured from the bottom-most edge of a line of weakness to the top-most edge of the inwardly-protruding portion of the mated zip-lock closure mechanism (e.g., top-most edge 15c, shown in FIG. 3B), not including the substrate 16. This ensures that there are sufficient margins of front and rear panel material above the zip-lock closure mechanism, following removal of the handle portion, for the consumer to grasp between thumbs and fingers of the hands, and pull the front and rear panels away from each other to disengage the respective zip-lock closure mechanism components and open the package, as in FIG. 4B, and may be particularly important when the zip-lock closure mechanism has inside opening resistance in the upper portions of the ranges specified above.

Figure 12:
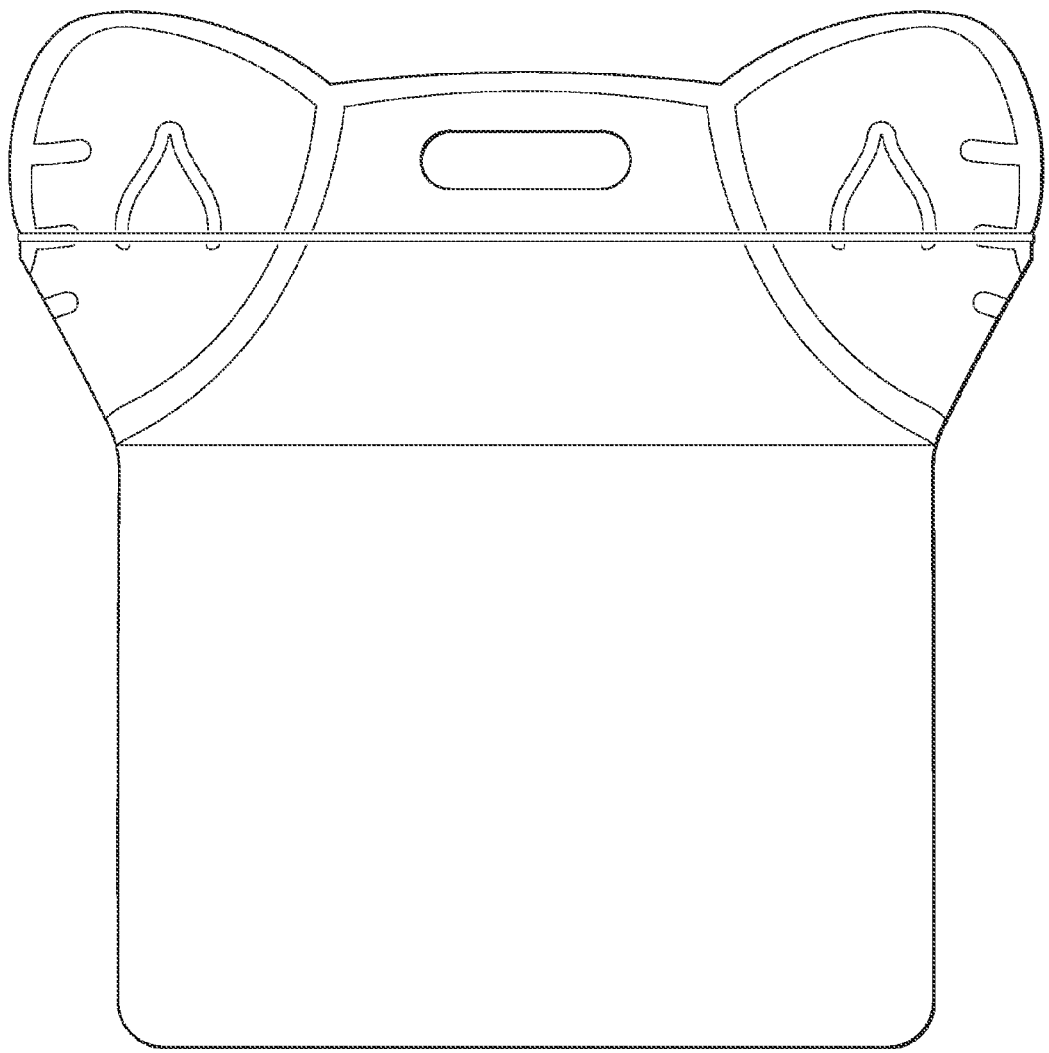
FIG. 12 is a schematic front view of a diaper package of one configuration.

A tear-away handle portion 60 may be used for various promotional purposes. For example, the tear-away handle portion 60 may be imprinted with suitable information so as to be used as an easily removable promotional item such as a proof of purchase, a coupon, a convenient informational note (bearing, e.g., product information, a web site address, telephone numbers, etc.) providing a preferable alternative to imprinting such items on the main portion of the package, which would require the consumer to cut them out. In further embodiments, lines or paths of weakness formed by, e.g., perforations or scoring, at least partially circumscribing such a promotional item for easy tear away may be included, in addition to the main line of weakness 17. The advantage thereby provided is that perforations or scoring providing for easy tear away of a promotional item may be included for consumer convenience but need not be placed on the main portion of the package, where they could compromise the package's structural integrity and dust/moisture barrier functionality. As in FIG. 12, the tear away handle portion may be provided with a certain dimension, either by itself or in coordination with the remainder of the package, featuring aesthetically pleasing elements for the consumer, such as objects, animals, characters, icons, etc.

Referring to FIG. 2, front and rear panels 20a, 20b may be joined at a second location above the zip-lock closure mechanism by a top seam 18. Top seam 18 may be line or path along the front and rear panels at which they are joined by a weld or line of adhesive material. A top seam 18 may be desired to provide tamper resistance during retail display and/or to provide secondary assurance that the package will not be prematurely opened prior to retail sale, in the event the zip-lock closure mechanism 15 prematurely gives way and opens. When the package includes line(s) of weakness 17 as described above, the portions including a top seam 18 may be torn away by the consumer when desired, exposing the zip-lock closure mechanism.

In another example, however, the package 10 may have the line(s) of weakness 17 omitted. In this example, the material of the front and rear panels about the handle cut 21 may remain in place to be used by the consumer to grasp and pull apart the front and rear panels to disengage the zip-lock closure mechanism components and open the package. In this example, if desired, a top seam 18 may be formed by a frangible weld, or a line or strip of releasable adhesive disposed between the front and rear panels above the zip-lock closure mechanism 15 may be substituted for a weld to serve one or more of the purposes for top seam 18 described above.

Still referring to FIG. 2, the film forming the front and/or rear panels of package 10 also may extend below a bottom seam 40 to form a bottom extension 41. Bottom extension 41 may have one or more wicket holes 42 therethrough. A bottom extension 41 with one or more wicket holes 42 therethrough may be used by handling and packing machinery to control, hold and/or advance the bag structure through the machinery, and may also be used by a retailer for, e.g., hanging the package from display hooks. In the latter event, it may be desired that an informational indicium 45 (such as trademark, trade name, descriptive words or numbers, etc.) be included on a panel so that it is easily legible (i.e. alphanumeric characters of the indicium positioned so that they read normally left-to-right, or top-to-bottom—as suggested in FIG. 2) when the bag is hung upside down (with handle and zip-lock opening at bottom).

The package described above provides a retail package of diapers that is convenient for one-handed carry. It also provides a package that may be opened and reclosed by the consumer, where reclosing is effective for keeping the unused supply of diapers in the package clean and dry for the time needed until they are used.

Test/Measurement Methods

In-bag Compression Measurement

In-bag Compression is measured by inserting a tab like pressure sensor into a packaging containing the diapers and reading out the pressure directly via MTS Insight 2 HS, as available from MTS Systems Corp., Eden Prairie, Minn.). All testing is performed in a conditioned room maintained at about 23° C.±2° C. and about 50%±2% relative humidity.

To prepare a specimen of a sample package, a rough circle having a diameter of approximately 5 cm is removed from the package to form a hole 70, the hole 70 positioned where the package is expected to receive the highest pressure, as in FIG. 1B. For the package configuration of FIG. 1B wherein the diapers are stacked as depicted in FIG. 11, the position where the package receives the highest pressure is believed to be toward the center of the diaper facing the inner surface of the package with the largest area.

The specimen package is then positioned such that the hole 70 faces up. The pressure sensor probe having 40 mm in diameter is inserted into hole 70 and compressed traveling down for 5 mm and held in place until reading is stabilized. The reaction force observed 30 minutes later is recorded.

Inside Opening Resistance Measurement

Inside opening resistance is measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. Both the movable (upper) and stationary (lower) pneumatic jaws are fitted with rubber faced grips, wider than the width of the test specimen. All testing is performed in a conditioned room maintained at about 23° C.±2° C. and about 50%±2% relative humidity.

Figure 8:
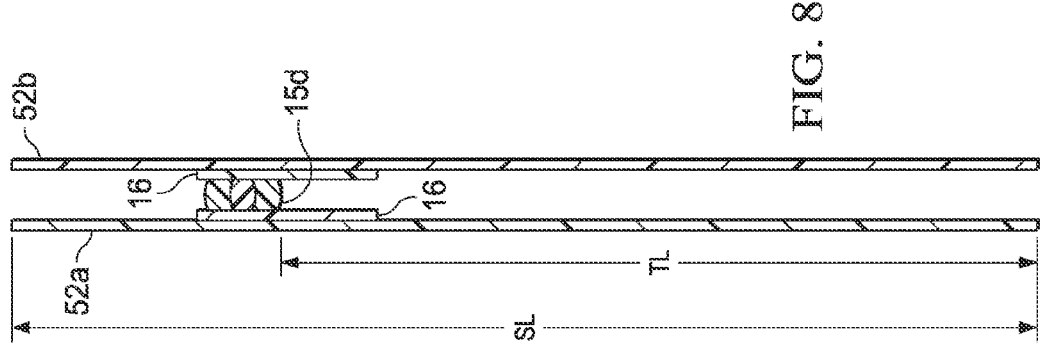
FIG. 8 is a schematic illustration of the cross section of a specimen as indicated in FIG. 7.
Figure 7:
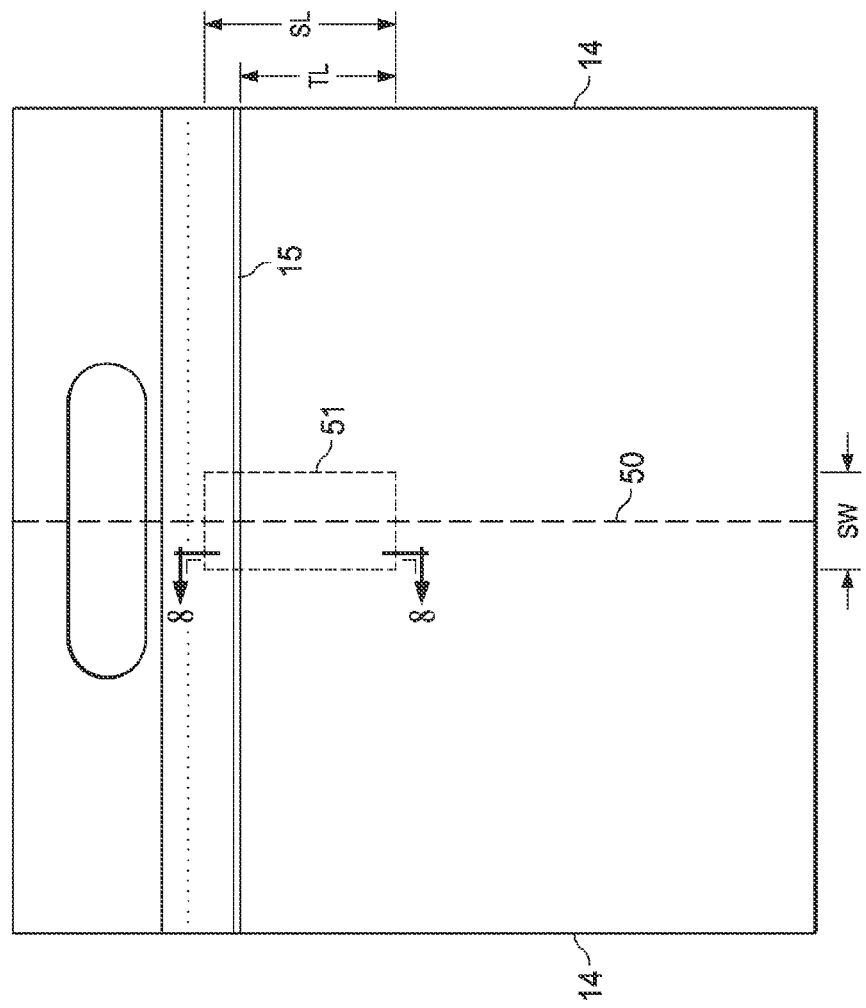
FIG. 7 is an illustration depicting the location and outline of a specimen on a package for Inside Opening Resistance measurement.

To prepare a specimen of a sample package with zip-lock closure mechanism for testing, empty the sample package of its contents, and lay it down open (zip-lock closure mechanism components disengaged) and flat on one of its front or rear panels on a work bench. Use a large flat object such as a board or book to press on the package to express air and substantially eliminate air spaces inside the package, and then engage and close the zip-lock closure mechanism components. Referring to FIG. 7, mark a line 50 on the upward-facing panel, perpendicular to and approximately bisecting the length of the zip-lock closure mechanism 15. Outline a rectangular specimen 51 on the upward-facing panel, 5.08 cm (±0.05 cm) (specimen length SL) by 2.54 cm (±0.05 cm) (specimen width SW) (SL dimension perpendicular to the length of the zip-lock closure mechanism 15), and located such that the specimen is longitudinally centered on line 50 and the zip-lock closure mechanism is located on the specimen as indicated in FIGS. 7 and 8, where TL is 40.4 mm (±0.05 cm) and is the tab length, measured from the lower edge of the specimen to the bottom-most edge of the inwardly-protruding portion of the mated zip-lock closure mechanism (e.g., bottom-most edge 15d, shown in FIG. 8), not including the substrate 16. Die-cut the specimen from the sample package so as to include substantially equally-sized facing portions of both front and rear panels and a section of the engaged closure mechanism 15, about the outline. This should yield a specimen having two tabs 52a, 52b which have been cut from the front and rear panels, joined by the section of the engaged closure mechanism, as suggested in FIG. 8. Condition the specimen inside the conditioned room for at least 24 hours prior to testing.

For analysis, set the gage length to 50.8 mm. Zero the crosshead and load cell. Insert one of the specimen tabs 52a, 52b approximately 1.50 cm into the upper grips, aligning it vertically within the upper and lower jaws and close the upper grips. Insert the other of the specimen tabs 52a, 52b approximately 1.5 cm into the lower grips and close the lower grips. After clamping in both grips the specimen should be under enough tension to eliminate any slack, but less than 0.05 N of force on the load cell. (Since bending the tabs 52a, 52b as reflected in FIG. 9 may affect their length, it is acceptable to adjust the gage length slightly as necessary and re-zero the crosshead and load cell after clamping the tabs in the grips, to accomplish the balance between elimination of slack and less than 0.05 N of tensile force in the specimen.) The manner in which the specimen is to be pulled in the test is illustrated in FIG. 9.

Program the tensile tester to perform an extension test, collecting force and extension data at an acquisition rate of 50 Hz as the crosshead raises at a rate of 100 mm/min until the section of zip-lock closure mechanism disengages (tabs 52*a*, 52*b* separate). Start the tensile tester and data collection. Program the software to record Peak Force (N) from the constructed force (N) verses extension (mm) curve. Calculate Inside Opening Resistance as:

Inside Opening Resistance=Peak Force (N)/width of specimen (cm)

Analyze all specimens in substantially identical manner. Record Inside Opening Resistance to the nearest 0.1 N/cm. A total of 10 specimens, taken one each from 10 sample packages, are analyzed. Calculate and report the average and standard deviation of Opening Resistance to the nearest 0.1 N/cm for the ten specimens.

Top Angle Measurement

Referring to FIGS. 10A, 10B and 11, to measure the respect top angles $\alpha_1$ and $\alpha_2$ formed by the respective upper portions of the front and rear panels with horizontal, provide the subject package in a substantially new condition, with none of its packaged stacked diaper contents removed. Ensure that the zip-lock mechanism is in its closed configuration. Obtain and provide a clamp having opposing clamping jaws 100*a*, 100*b* that are at least as long as the openable length ZL of the zip-lock mechanism of the package. Suspend the clamp with the length of the clamping jaws disposed horizontally, at a height sufficient to completely suspend the package from the clamp. Insert the top of the package including the zip-lock mechanism into the clamping jaws, to a depth sufficient to substantially align the bottom-most edge of the inwardly-protruding portion of the mated zip-lock mechanism with the bottom-most inner edges of the clamping jaws, and clamp the jaws together with a force/pressure sufficient to grip and suspend the package without causing permanent deformation of the zip-lock mechanism.

Measure Top Angles $\alpha_1$ and $\alpha_2$ using a protractor referenced to horizontal, by sighting along the planes approximated by the respective upper portions of the front and rear panels 20*a*, 20*b* with horizontal, where they extend between the respective upper front and rear edges of the stack of contained diapers 30 and the bottom-most edge of the inwardly-protruding portion of the mated zip-lock mechanism 15.

Measure Top Angles $\alpha_1$ and $\alpha_2$ as described above for 10 sample packages, and calculate the averages, for purposes of further calculations.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package containing disposable diapers, comprising:
a bag having front and rear panels formed of polymer film, each of the panels having an inner surface and an outer surface, the bag also having a bottom end portion at which the front and rear panels are directly or indirectly joined by one or more welds, and a top end portion that is openable and recloseable,
the top end portion comprising:
a first zip-lock component joined to the inner surface of the front panel, and
an opposing second zip-lock component joined to the inner surface of the rear panel,
the first and second zip-lock components being cooperative and operable to engage each other and hold the top end portion closed, and to disengage each other and allow the top end portion to open, to enable the top end portion to be repeatedly opened and reclosed by a user; and
respective top extending portions of the front and rear panels each extending upwardly beyond the zip-lock components, the top extending portions each having a handle cut therethrough; wherein the top extending portions have a top seam joining them together, the top seam being disposed between the handle cuts and the zip-lock components;
wherein the first and second zip-lock components in a closed configuration have an inside opening resistance of from 0.79 N/cm to 48 N/cm as determined by the Inside Opening Resistance Measurement Method as defined herein.

2. The package of claim 1 wherein the package has an in bag compression of from 1000 Pa to 10000 Pa as determined by the In Bag Compression Measurement Method as defined herein.

3. The package of claim 1 wherein the package has a top angle of from 5 to 75 degrees as determined by the Top Angle Measurement Method as defined herein.

4. The package of claim 1 wherein the polymer film is formed of a layer of polyethylene and the layer of polyethylene constitutes at least 90 percent of the caliper of the polymer film.

5. The package of claim 1 wherein the polymer film is formed of a layer of polyethylene and a layer of polypropylene.

6. The package of claim 1 wherein the top extending portions each have a line of weakness therein, disposed between the handle cut and the zip-lock components.

7. The package of claim 6 wherein the top extending portions have a longitudinal dimension of at least 5 mm between the interface between the respective zip-lock components in a closed configuration, and the line of weakness, along a vertical centerline of the package.

8. The package of claim 1 wherein the polymer film and the zip-lock components are each formed of at least 50 percent by weight of the same polymer.

9. The package of claim 8 wherein the polymer is polyethylene.

10. The package of claim 6 wherein at least one of the top extending portions have a promotional item selected from the group of proof of purchase, coupon, or informational note, and combinations thereof, imprinted thereon.

11. The package of claim 10 wherein the promotional item is at least partially circumscribed by an additional line of weakness.

12. The package of claim 6 wherein the line of weakness has an average tear resistance of from 10 N to 50 N.

* * * * *